United States Patent
Sinofsky

Patent Number: 5,947,959
Date of Patent: Sep. 7, 1999

[54] PHOTOTHERAPEUTIC APPARATUS WITH DIFFUSIVE TIP ASSEMBLY

[75] Inventor: Edward L. Sinofsky, Dennis, Mass.

[73] Assignee: Rare Earth Medical, Inc., West Yarmouth, Mass.

[21] Appl. No.: 08/991,130

[22] Filed: Dec. 16, 1997

Related U.S. Application Data

[63] Continuation-in-part of application No. 08/827,631, Apr. 10, 1997, which is a continuation-in-part of application No. 08/303,605, Sep. 9, 1994.

[51] Int. Cl.$^6$ .................................................. A61B 17/36
[52] U.S. Cl. .................................. 606/15; 606/17; 606/13
[58] Field of Search .............................. 606/7–10, 13–17; 607/88, 89

[56] References Cited

U.S. PATENT DOCUMENTS

| | | | |
|---|---|---|---|
| 5,151,096 | 9/1992 | Khoury | 606/17 |
| 5,151,097 | 9/1992 | Daikuzono | 606/16 |
| 5,163,935 | 11/1992 | Black et al. | 606/7 |
| 5,219,346 | 6/1993 | Wagnieres et al. | 606/16 |
| 5,431,647 | 7/1995 | Purcell, Jr. et al. | 606/16 |
| 5,441,497 | 8/1995 | Narciso | 606/15 |
| 5,536,265 | 7/1996 | Van den Bergh et al. | 606/16 |
| 5,643,253 | 7/1997 | Baxter et al. | 606/17 |

FOREIGN PATENT DOCUMENTS

| | | | |
|---|---|---|---|
| 96/07451 | 3/1996 | WIPO | A61N 5/06 |

*Primary Examiner*—Robert L. Nasser
*Attorney, Agent, or Firm*—Thomas J. Engellenner; Nutter, McClennen & Fish, LLP

[57] ABSTRACT

Methods and devices are disclosed in which a dielectric structure is operatively coupled to phototherapeutic instrument to reflect light without substantial heating. The invention is particularly useful in light diffusive tip assemblies for phototherapy that have components which increase in temperature after prolonged exposure to light, such as metallic plugs or coatings typically located at the end cap of the diffusive tip assembly to terminate light propagation, and also metallic structures incorporated into phototherapeutic instruments to facilitate radiographic or fluoroscopic imaging during a therapeutic procedure.

17 Claims, 2 Drawing Sheets

PHOTOTHERAPEUTIC APPARATUS WITH DIFFUSIVE TIP ASSEMBLY

REFERENCE TO RELATED APPLICATIONS

This application is a continuation-in-part of U.S. patent application Ser. No. 08/827,631, incorporated herein by reference and filed Apr. 10, 1997, which is a continuation-in part of U.S. patent application Ser. No. 08/303,605, incorporated herein by reference and filed Sep. 9, 1994.

BACKGROUND OF THE INVENTION

The technical field of this invention is phototherapy and, in particular, methods and devices employing optical fibers or other flexible light waveguides to deliver radiation to targeted biological sites.

Fiber-optic phototherapy is an increasingly popular modality for the diagnosis and/or treatment of a wide variety of diseases. For example, in surgery, infrared laser radiation is often delivered to a surgical site by an optically transmissive fiber in order to coagulate blood vessels or cauterize tissue. Similar fiber-optic delivery systems have been proposed for endoscopic or catheter-based instruments to deliver therapeutic radiation to a body lumen or cavity. U.S. Pat. No. 4,878,492 to Sinofsky teaches the use of infrared light to illuminate the endothelial lining of a blood vessel during balloon angioplasty. U.S. Pat. No. 5,053,033 to Clarke teaches the use of ultraviolet light to prevent the proliferation of smooth muscle cells at an angioplasty site.

Fiber-optic irradiation has also been used to activate remote chemical agents with a patient's body. It is well known that light can promote photochemical reactions which, in the absence of light, would proceed either very slowly or not at all. The use of light to activate chemical agents within a patient is often referred to as "photodynamic therapy." For example, U.S. Pat. No. 4,336,809 (Clark) and U.S. Reissue Pat. No. RE 34,544 (Spears) disclose that hematoporphyrin dyes and the like selectively accumulate in tumorous tissue and that cancerous tissue that has taken up the dye can be preferentially destroyed by radiation (typically high intensity red light) absorbed by the dye molecules during phototherapy.

It has also been desirable to promote photothermal treatment for a variety of diseases. This involves the delivery of optical energy to the desired site and the conversion of that optical energy into thermal energy. The intense heat thus generated can cause undesired tissue to undergo necrosis or to separate from a substrate layer. In addition, high energy, rapidly pulsed laser radiation has also been proposed for essentially non-thermal ablation of tissue.

Typically, light can be delivered to the site of the desired phototherapeutic reaction by inserting a fiber-optic cable into a patient and maneuvering it to the site of the desired photochemical reaction. The position of the fiber's tip can be monitored by including a metallic structure at the tip and monitoring the position of the metallic structure, either visually or by x-ray fluoroscopy. Additionally, metallic structures are sometimes used to reflect light and to thereby control the illumination field within the patient.

When illuminated by light, these metallic structures absorb a small, yet significant amount of optical energy and reradiate it as heat. Since the metallic structures of phototherapeutic instruments are generally in contact with or proximate to surrounding tissue, the rise in temperature of these structures can inflict heat-induced tissue damage on surrounding tissue or melt catheters in the vicinity of the fiber's tip.

Accordingly, there exists a need for better methods and apparatuses for preventing the metallic structure in phototherapeutic devices from being heated excessively by incident light during use.

SUMMARY OF THE INVENTION

Methods and devices are disclosed in which a dielectric structure is operatively coupled to a phototherapeutic instrument to reflect light without substantial heating. The invention is particularly useful in light diffusive tip assemblies for phototherapy that have components which increase in temperature after prolonged exposure to light, such as metallic plugs or coatings typically located at the end cap of the diffusive tip assembly to terminate light propagation, and also in metallic structures incorporated into phototherapeutic instruments to facilitate radiographic or fluoroscopic imaging and direct visualization of the diffusive tip assembly during a therapeutic procedure.

Typically, diffusive tip assemblies include a light-transmissive housing forming a chamber filled with a diffusive medium and extending along a longitudinal axis. At its proximal end, the housing is adapted to receive a fiber-optic cable. A reflector component is often disposed at the distal end of the chamber. In the present invention, the reflector component includes a dielectric reflector structure.

The dielectric reflector structure of the invention includes at least one dielectric layer having an interface at its proximal end with the diffusive medium and forming a proximal reflecting surface. The distal end of the dielectric layer forms a distal reflecting surface at the interface between the dielectric layer and either a second dielectric layer or a light-transmissive substrate layer. The substrate layer is adjacent to a thermally susceptible surface such as a conducting surface. The dielectric structure essentially creates a gradient in the index of refraction. By proper choice of materials and their thicknesses, the dielectric gradient structure achieves nearly complete reflection without substantial heating. As used herein, the terms "nearly complete reflection" and/or "complete reflection" are intended to encompass reflectivity ratios of 95 percent or greater. Similarly, the term "without substantial heating" is intended to encompass temperature rises during operation that do not exceed 60° C.

In the operation of a light diffuser according to the invention, light carried by the fiber-optic cable enters the chamber at its proximal end and propagates distally through the diffusive medium in the chamber toward the dielectric reflector structure. At the dielectric reflector structure, the proximal reflecting surface reflects a portion of the light incident thereon back into the diffuser and transmits the remaining portion of the light incident thereon distally, thereby attenuating the intensity of illumination incident on the distal reflecting surface. Since the dielectric layer typically has a purely real index of refraction, no heating occurs in the dielectric.

This incident light transmitted through the proximal reflecting surface is then reflected by the distal reflecting surface of the dielectric layer. The position of this distal reflecting surface relative to the proximal reflecting surface is chosen such that the light reflected by the distal reflecting surface and the light reflected by the proximal reflecting surface constructively interfere with one another. This increases the intensity of the light propagating proximally and reduces the intensity of the light propagating distally.

Where the distal reflecting surface is an interface between the dielectric layer and a thermally susceptible surface, such as a conducting surface, it is apparent that, because the proximal reflecting surface transmits only a portion of the light incident thereon distally toward the thermally susceptible surface, the intensity of the light incident on the thermally susceptible surface is attenuated by the reflection at the proximal reflecting surface. As a result, there is less energy available for the undesired heating of the thermally susceptible surface.

Although the scope of the invention includes the case of a single dielectric layer, as set forth above, such a configuration may not result in sufficient attenuation of the optical energy incident on the thermally susceptible surface. Consequently, in one preferred embodiment, a plurality of adjacent dielectric layers is interposed between the diffusive medium and the thermally susceptible surface. Each such dielectric layer forms a proximal reflecting surface which proximally reflects a portion of the field incident thereon. For each such dielectric layer, a remaining portion of the field incident thereon is transmitted distally towards either an adjacent dielectric layer or, in the case of the most distal such layer, towards a thermally susceptible surface. The cumulative effect of a plurality of adjacent dielectric layers on the light passing therethrough is a significant attenuation of the light intensity illuminating the thermally susceptible surface resulting from each of the reflections occurring at each dielectric interface.

In another embodiment of the invention, the thermally susceptible surface is an annular structure. In this embodiment, the first reflection can be provided by an annular interface between the diffusive medium and a cylindrical dielectric layer interposed between the illumination source and the annular, thermally susceptible surface. Succeeding reflections can then be provided by annular interfaces between adjacent cylindrical dielectric layers. In this embodiment, the succession of adjacent dielectric layers interposed between the illumination source and the thermally susceptible surface forms a tube having a lumen filled with the diffusive medium.

BRIEF DESCRIPTION OF THE FIGURES

These and other features, aspects and advantages of the invention will be better understood with reference to the following description, the appended claims, and the accompanying drawings in which:

DETAILED DESCRIPTION

Figure 1:
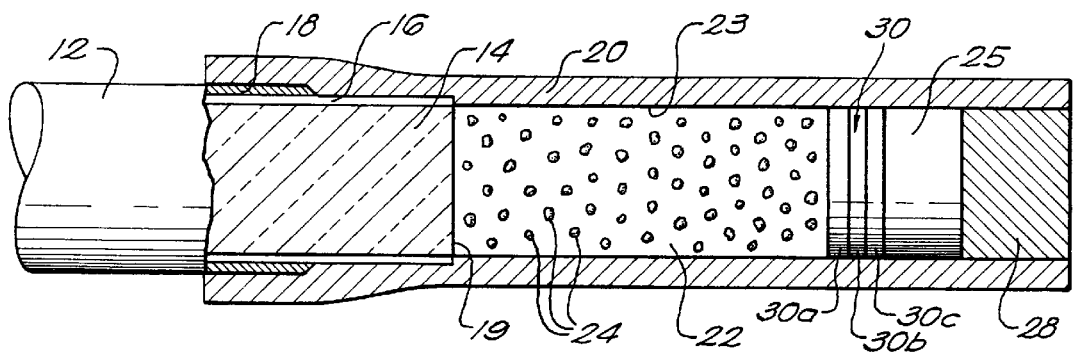
FIG. 1 shows a cut-away view of a diffusive tip assembly according to the invention in which a plurality of dielectric layers is interposed between the diffusive medium and an end plug.

FIG. 1 depicts a diffusive tip assembly 10 which includes an optical fiber 12 having a fiber-optic core 14, a cladding layer 16 circumferentially disposed around the core 14, and an outer buffer coating 18 circumferentially disposed around the cladding layer. The fiber-optic core 14 extends along a longitudinal axis into the proximal end of a light-transmissive housing 20 before terminating in an end face 19. The housing 20 extends along the longitudinal axis past the end face 19 and forms a light-transmissive wall 23 of a tubular chamber 21 having a radius comparable to the radius of the optical fiber 12. The tubular chamber 21 is bounded on its side by the light transmissive wall 23, on its proximal end by the end face 19 of the fiber-optic core 14 and on its distal end by a dielectric reflector 30. A diffusive medium 22 having individual scattering particles 24 suspended throughout fills the tubular chamber 21. Preferably, the diffusive medium 22 has a greater index of refraction than the housing wall 23.

Figure 4:
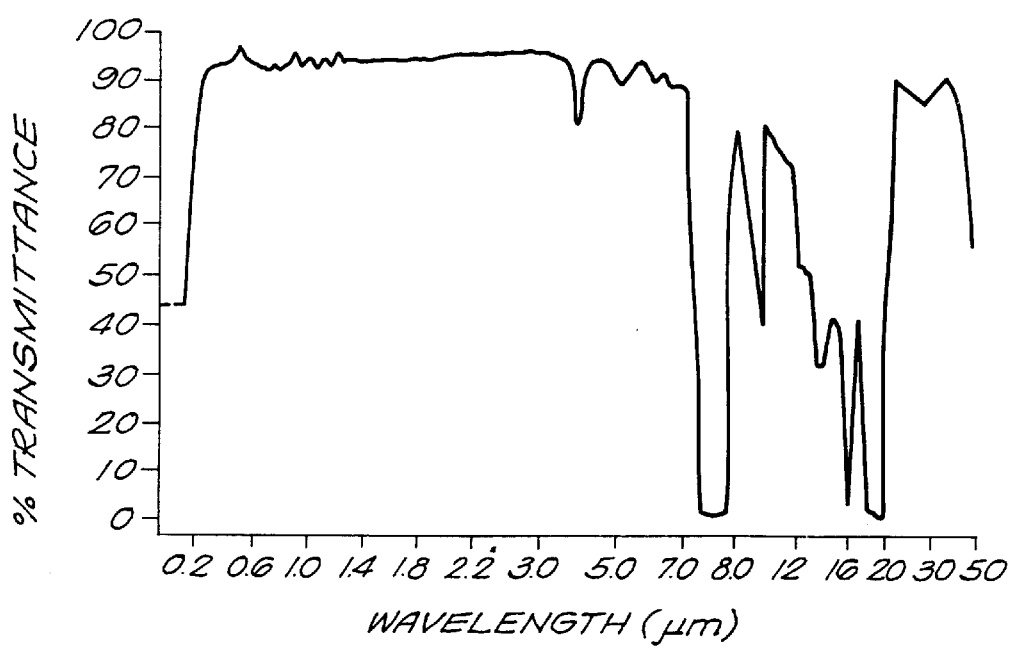
FIG. 4 shows the transmission spectrum of the wall of the tubular chamber shown in FIG. 1.

In one preferred embodiment, the diffusive tip assembly 10 shown in FIG. 1 has a Teflon® FEP tubular housing having an outer diameter of about 0.5 millimeters and an inner diameter of about 0.25 millimeters. The transmission spectrum of Teflon® FEP, as shown in FIG. 4, indicates that this material is well suited for use as a housing wall for transmitting a broad spectrum of light, from infrared to ultraviolet.

The tubular chamber 21 is injected with a diffusive medium 22, such as silicone, epoxy or other polymer. A liquid diffusive medium 22 can be used to extend phototherapy into ultraviolet and infrared wavelengths. In particular, deuterium oxide and other heavy water solutions are useful for transmitting infrared light with low losses and minimal heating. In either case, the tubular chamber 21 should be completely filled with the diffusive medium 22 to avoid entrapment of air bubbles.

In one preferred embodiment, the tubular chamber 21 is filled with a diffusive medium 22 formulated by mixing seventy parts of clear silicone, Mastersil™ formula 151-Clear (available from Masterbond, Inc. of Hackensack, N.J.) with one part of titania filled silicone, Mastersil™ formula 151-White (also available from Masterbond). This results in a diffusive tip assembly 10 which uniformly transmits light at about 633 nanometers.

The concentration of scattering particles 24 incorporated into the diffusive medium 22 can be adjusted to meet particular applications. Table 1 below shows relevant characteristics for three different types of scattering particles 24. In certain applications it may desirable to achieve blended characteristics by mixing two or more types of scattering particles 24 together.

TABLE 1

Scatterer Characteristics

| Scatterer Composition | Density (gram/cc) | Transmission Spectrum ($\lambda$ in mm) |
|---|---|---|
| $TiO_2$ | 4.0 | .45–11 |
| $SiO_2$ | 2.1 | .2–7 |
| $Al_2O_3$ | 3.6 | .2–9 |

The illustrated dielectric reflector 30 comprises a plurality of dielectric interfaces formed by dielectric layers 30a, 30b, 30c on a substrate layer 25. The substrate layer 25 is a light-transmissive layer such as glass. To ensure constructive interference within the dielectric layer, each dielectric layer is a quarter wavelength thick as measured by the wavelength within the dielectric layer (i.e. nd=$\lambda$/4 where n=index of reflection and d=thickness of dielectric layer). It is apparent, however, that thicknesses that are integer multiples of a quarter wavelength will likewise produce the desired constructive interference within the dielectric layer. In one preferred embodiment, the dielectric reflector 30 includes fifteen to thirty dielectric layers. In another preferred embodiment, the dielectric reflector 30 can include six to thirty dielectric layers.

Preferably, the proximal dielectric layer 30a has a dielectric constant larger than the dielectric constant of the diffusive medium 22. The dielectric constants for succeeding dielectric layers 30b, 30c need only be different from each other so as to ensure the existence of a reflection at the dielectric interfaces. In one preferred embodiment, the dielectric used for the first, or proximal, dielectric layer 30a is used for all odd number layers and the dielectric used for the second dielectric layer 30b is used for all even number layers. Although any dielectric material having the foregoing properties can be used, one preferred embodiment employs two dielectrics that are rare earth oxides. Alternatively, the dielectric can be selected from a group consisting of silicon dioxide, titanium dioxide, and silica oxide.

Light propagating distally along the longitudinal axis through the fiber-optic core 14 enters the diffusive medium 22 at the proximal end of the tubular chamber 21 and scatters off the individual scattering particles 24 before reaching the light-transmissive wall 23 of the housing. If this scattered light is incident on the wall 23 at an angle exceeding the critical angle for internal reflection for the interface between the wall 23 and the diffusive medium 22, the light exits the diffusive tip assembly 10.

Any light that does not exit the diffusive tip assembly 10 continues toward the distal end of the tubular chamber 21 where it impinges upon the proximal dielectric layer 30a. The proximal dielectric layer 30a reflects a portion of the light incident thereon back toward the proximal end of the tubular chamber 21. The remaining portion of this incident light propagates through the proximal dielectric layer 30a until it reaches the second dielectric layer 30b. At the second dielectric layer 30b, a portion of the remaining incident light is reflected back toward the proximal end of the tubular chamber 21 and a further remaining portion continues to propagate distally through the second dielectric layer 30b.

The sequence of reflections at each dielectric interface proceeds as described above until light propagates through the distal dielectric layer 30c and reaches a metal slug 28. The metal slug, which is preferably a gold slug, then reflects a portion of the light incident thereon back toward the proximal end of the tubular chamber 21. The remaining portion of the incident light is converted into heat at the metal slug 28. It is the reduction of this heat and of the accompanying risk of heat-induced tissue damage that is the object of this invention.

It is apparent that as light propagates distally through the dielectric reflector 30, the magnitude of the Poynting vector associated with the light wave decreases. In the apparatus described above, the magnitude decreases stepwise with each reflection at each dielectric interface. As a result, the magnitude of the Poynting vector associated with light propagating through the substrate layer 25 adjacent to the metal slug 28, and therefore the power incident on the metal slug 28 itself, is significantly lower than the magnitude of the Poynting vector associated with the light propagating through the diffusive medium 22. With less energy incident upon it, the metal slug 28 does not increase its temperature past the point at which heat-induced tissue damage occurs. Consequently, heat-induced tissue damage is avoided.

Figure 2:
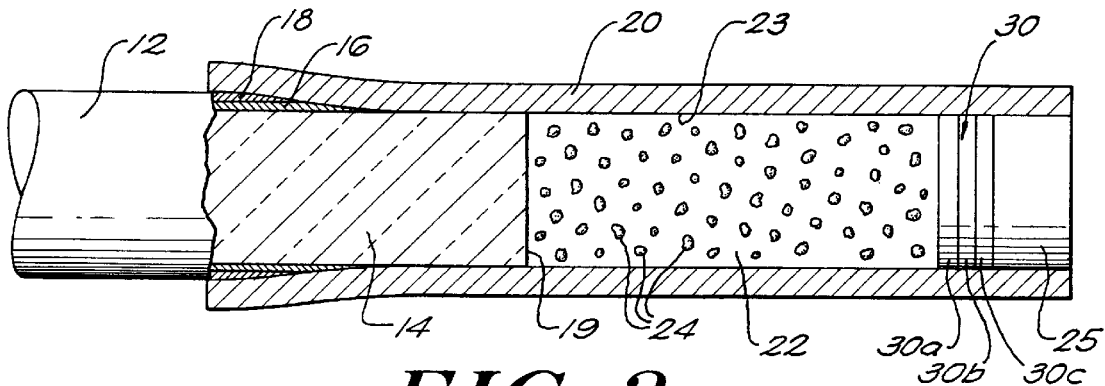
FIG. 2 is a close-up view of an alternative embodiment in which the metal slug shown in FIG. 1 is removed.

For applications in which it is unnecessary to monitor the position of the tip of the diffusive tip assembly 10, the metal slug 28 is not necessary and can be dispensed with as shown in FIG. 2. The reflecting function provided by the metal slug 28 in the embodiment shown in FIG. 1 is instead performed by the dielectric reflector 30. Since the dielectric reflector 30 is comprised of materials having no imaginary component of index of refraction, no absorptive heating occurs within it. As a result, the dielectric reflector 30 can prevent light from escaping through the distal end of the tubular chamber 21 without a corresponding increase in temperature sufficient to cause heat damage to surrounding tissue.

Figure 3A:
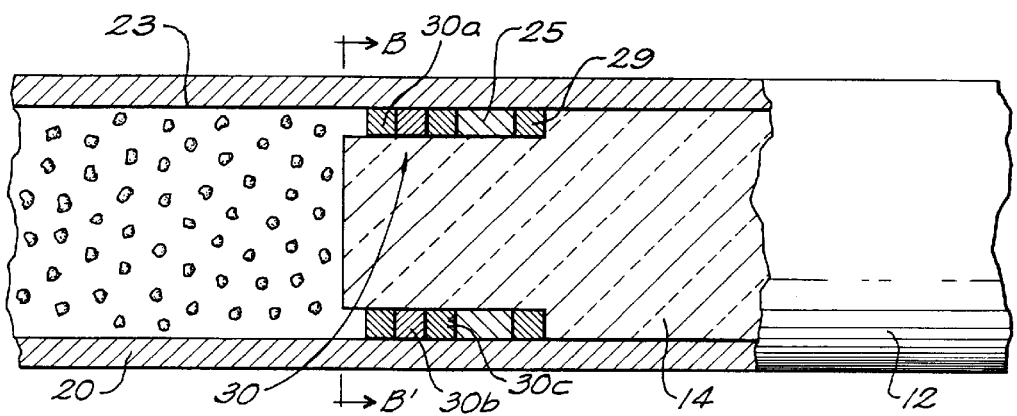
FIG. 3A shows an embodiment similar to that shown in FIG. 2 in which the metal slug, the glass substrate, and the plurality of dielectric layers are cylindrical and circumferentially disposed around the diffusive medium.

In certain endoscopic applications, it is also of interest to locate a point on the diffusive tip assembly 10 other than the tip. For these applications, the dielectric reflector 30 can be an annular structure comprised of a series of dielectric layers 30a, 30b, 30c on an annular substrate layer 25 as shown in FIG. 3A and in cross-section in FIG. 3B. In this embodiment, a radiographic marker such as a metal collar 29 is adjacent to an annular substrate layer 25. The fiber optic core 14 extends into the interior of the annulus and into the diffusive medium 22 that fills the tubular chamber 21.

Figure 3B:
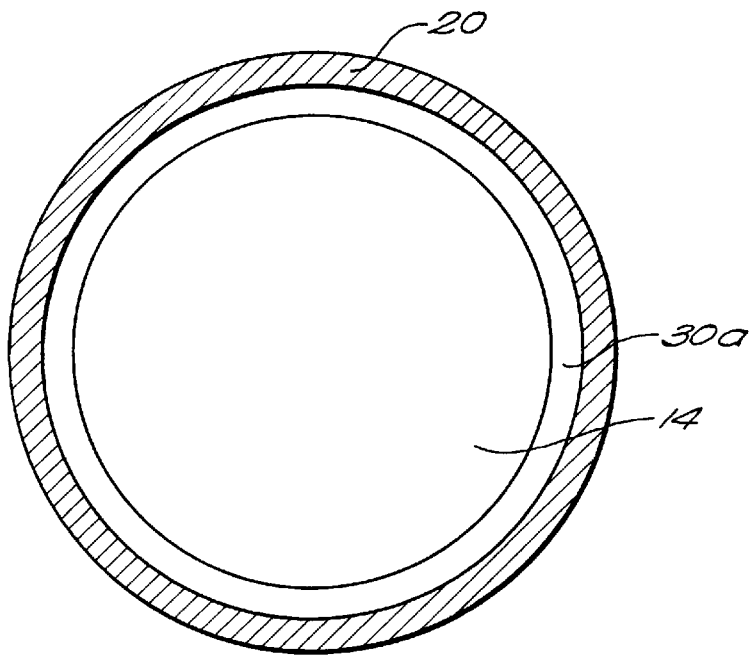
FIG. 3B is a cross-section of the structure depicted in FIG. 3A.

In the embodiment shown in FIGS. 3A and 3B, the undesired heating of the metal collar 29 is reduced by shielding it with a dielectric reflector 30 in the same manner as that described above in connection with FIG. 1. Since the dielectric reflector 30, like the metal collar 29, is annular, light can propagate through the center of the annulus formed by the dielectric reflector 30 and the metal collar 29 with minimal interference. Simultaneously, light incident on the metal collar 29 is significantly attenuated by the dielectric reflector 30. Consequently, the undesired heating of the metal collar 29 is reduced.

It will thus be seen that the invention efficiently attains the objects set forth above. Since certain changes may be made in the above construction without departing from the scope of the invention, it is intended that all matter contained in the above description or shown in the accompanying drawings be interpreted as illustrative and not limiting.

It is also to be understood that the following claims are intended to cover all generic and specific features of the invention described herein. When describing the invention, what is claimed as new and secured by Letters Patent is:

1. A diffusive tip assembly for illuminating a lumen, said diffusive tip assembly comprising:

a light transmissive housing forming a chamber having a proximal end adapted to receive a light-transmitting optical fiber and a distal end separated from said proximal end along a longitudinal axis, said chamber containing a diffusive medium characterized by a first dielectric constant; and a dielectric reflector structure mounted in said chamber, said dielectric reflector structure including at least one dielectric layer characterized by a second dielectric constant different from said first dielectric constant, said dielectric layer including a proximal reflecting surface adapted for illumination by light transmitted through said diffusive medium and for formation of a first reflected field and a transmitted field, and a distal reflecting surface parallel to said proximal reflecting surface adapted for illumination by said transmitted field and for formation of a second reflected field, said second reflected field constructively interfering with said first reflected field.

2. The diffusive tip assembly of claim 1 wherein said proximal reflecting surface comprises a dielectric interface between said diffusive medium and said at least one dielectric layer.

3. The diffusive tip assembly of claim 2 wherein said distal reflecting surface comprises a further interface between said at least one dielectric layer and a further dielectric layer, said further dielectric layer chosen to have a further dielectric constant different from said second dielectric constant.

4. The diffusive tip assembly of claim 2 wherein said distal reflecting surface comprises a further interface between said at least one dielectric layer and a conducting medium.

5. The diffusive tip assembly of claim 4 wherein said chamber is tubular.

6. The diffusive tip assembly of claim 1 wherein said at least one dielectric layer comprises a rare earth oxide.

7. The diffusive tip assembly of claim 1 wherein said at least one dielectric layer comprises a dielectric from a group consisting of silicon dioxide, titanium dioxide, and silica oxide.

8. The diffusive tip assembly of claim 1 wherein said dielectric reflector structure further comprises a plurality of dielectric layers in optical communication with said at least one dielectric layer.

9. The diffusive tip assembly of claim 8 wherein said plurality of dielectric layers includes six to thirty dielectric layers.

10. The diffusive tip assembly of claim 1, wherein said dielectric reflector structure is an annular structure.

11. The diffusive tip assembly of claim 10, wherein said dielectric reflector structure further comprises a plurality of parallel, adjacent dielectric layers.

12. The diffusive tip assembly of claim 11 wherein said plurality of dielectric layers includes between six and thirty dielectric layers.

13. A diffusive tip assembly for illuminating a lumen with light at a predefined frequency, said diffusive tip assembly comprising:
   a light transmissive housing forming a chamber having a proximal end adapted to receive a light-transmitting optical fiber and a distal end separated from said proximal end along a longitudinal axis, said chamber containing a diffusive medium characterized by a first dielectric constant; and
   a dielectric reflector structure mounted in said chamber, said dielectric reflector structure including at least one dielectric layer characterized by a second dielectric constant different from said first dielectric constant, wherein said at least one dielectric layer has an optical thickness equal to an integral number of quarter wavelengths, said wavelength being a function of said predefined frequency.

14. A diffusive tip assembly for illuminating a lumen, said diffusive tip assembly comprising:
   a light transmissive housing forming a chamber having a proximal end adapted to receive a light-transmitting optical fiber and a distal end separated from said proximal end along a longitudinal axis, said chamber containing a diffusive medium characterized by a first dielectric constant; and
   a dielectric reflector structure mounted in said chamber, said dielectric reflector structure including at least one dielectric layer characterized by a second dielectric constant different from said first dielectric constant,
   wherein said dielectric reflector structure further comprises a plurality of dielectric layers in optical communication with said at least one dielectric layer.

15. The diffusive tip assembly of claim 14 wherein said plurality of dielectric layers includes six to thirty dielectric layers.

16. A diffusive tip assembly for illuminating a lumen, said diffusive tip assembly comprising:
   a light transmissive housing forming a chamber having a proximal end adapted to receive a light-transmitting optical fiber and a distal end separated from said proximal end along a longitudinal axis, said chamber containing a diffusive medium characterized by a first dielectric constant; and
   a dielectric reflector structure mounted in said chamber, said dielectric reflector structure including a plurality of parallel dielectric layers, at least one dielectric layer characterized by a second dielectric constant different from said first dielectric constant, and
   wherein said dielectric reflecting structure forms an annular collar circumferentially disposed around said fiber and in optical communication with said diffusive medium to reflect light propagating out of said diffusive medium back into said diffusive medium.

17. The diffusive tip assembly of claim 16 wherein said plurality of dielectric layers includes between six and thirty dielectric layers.

* * * * *